United States Patent
Johnson et al.

(10) Patent No.: US 9,808,182 B2
(45) Date of Patent: Nov. 7, 2017

(54) BREATHING DETECTION APPARATUS (71) Applicant: Bohnas LLC, Henderson, NV (US)

(72) Inventors: Casey Johnson, Coeeur d'Alene, ID (US); Greg Bauer, Post Falls, ID (US); Doran Thomas, Post Falls, ID (US)

(73) Assignee: Bohnas LLC, Henderson, NV (US)

( * ) Notice: Subject to any disclaimer, the term of this patent is extended or adjusted under 35 U.S.C. 154(b) by 265 days.

(21) Appl. No.: 14/664,611

(22) Filed: Mar. 20, 2015

(65) Prior Publication Data

US 2016/0270692 A1    Sep. 22, 2016

(51) Int. Cl.
*A61B 5/097* (2006.01)
*A61B 5/083* (2006.01)
(Continued)

(52) U.S. Cl.
CPC ............ *A61B 5/097* (2013.01); *A61B 5/0836* (2013.01); *A61B 5/7405* (2013.01);
(Continued)

(58) Field of Classification Search
CPC ..... A61B 5/097; A61B 5/0836; A61B 5/7405; A61M 16/085; A61M 16/0672;
(Continued)

(56) References Cited

U.S. PATENT DOCUMENTS

| | | |
|---|---|---|
| 3,643,660 A | 2/1972 | Hudson et al. |
| 4,201,205 A | 5/1980 | Bartholomew |

(Continued)

FOREIGN PATENT DOCUMENTS

| | | |
|---|---|---|
| EA | 004670 B1 | 6/2004 |
| WO | WO2006106328 A1 | 10/2006 |

OTHER PUBLICATIONS

"Biomarkers and Measurement of Risks: Concepts and Principles", Gigienicheskie kriterii sostoyaniya okruzhayuschei sredy 155. Vsemirnaya organizatsiya zdravookhraneniya, Aheneva, 1996, p. 50, lines 11-41, p. 51, lines 1-29.

(Continued)

*Primary Examiner* — Charles A Marmor, II
*Assistant Examiner* — Andrey Shostak
(74) *Attorney, Agent, or Firm* — Lee & Hayes, PLLC (57) ABSTRACT

An apparatus including a tubular channel having a pathway extending between a proximal end and a distal end of the tubular channel. The proximal end is configured to connect directly or indirectly to an end tidal $CO_2$ monitor. The distal end has an opening. The apparatus further includes a detection member including a chamber disposed in fluid communication with the pathway of the tubular channel such that gas entering the tubular channel via the opening on the distal end passes into the chamber. A detection element is disposed within the chamber and includes a component that is sensitive to one or more systemic biomarkers such that, upon exposure to a predetermined concentration level of the one or more systemic biomarkers contained in the gas, a state of the detection element experiences a permanent alteration and the detection member indicates that the predetermined concentration level of the one or more systemic biomarkers is present in the gas.

18 Claims, 9 Drawing Sheets

(51) Int. Cl.
*A61B 5/00* (2006.01)
*A61M 16/08* (2006.01)
A61M 16/06 (2006.01)
A61M 16/04 (2006.01)
A61M 16/16 (2006.01)

(52) U.S. Cl.
CPC ....... *A61M 16/085* (2014.02); *A61M 16/0666* (2013.01); *A61M 16/0672* (2014.02); *A61M 16/161* (2014.02); *A61M 2016/0413* (2013.01); *A61M 2205/0227* (2013.01); *A61M 2205/273* (2013.01); *A61M 2205/581* (2013.01); *A61M 2205/587* (2013.01); *A61M 2205/588* (2013.01); *A61M 2230/432* (2013.01)

(58) Field of Classification Search
CPC ........ A61M 16/161; A61M 2016/0413; A61M 2205/0227; A61M 2205/273; A61M 2205/581; A61M 2205/587; A61M 2205/588; A61M 2230/432; A61M 16/0666
See application file for complete search history.

(56) References Cited

U.S. PATENT DOCUMENTS

| | | |
|---|---|---|
| 5,474,060 A | 12/1995 | Evans |
| 5,849,594 A | 12/1998 | Balderson et al. |
| 6,247,470 B1 | 6/2001 | Ketchedjian |
| 6,502,573 B1 * | 1/2003 | Ratner ................ A61M 16/208 128/202.22 |
| 7,418,965 B2 | 9/2008 | Fukunaga et al. |
| 7,500,482 B2 | 3/2009 | Biederman |
| 7,640,932 B2 | 1/2010 | Curti et al. |
| 8,720,445 B2 | 5/2014 | Cain et al. |
| 2003/0229295 A1 * | 12/2003 | Houde .................... A61F 2/013 600/585 |
| 2004/0163648 A1 | 8/2004 | Burton |
| 2008/0260302 A1 * | 10/2008 | Martinez ............ B65D 33/1625 383/78 |
| 2008/0275427 A1 * | 11/2008 | Sage ................ A61M 25/0014 604/533 |
| 2010/0317956 A1 * | 12/2010 | Kartush ............... A61B 5/4041 600/380 |
| 2011/0199220 A1 * | 8/2011 | McAlister .............. B01J 19/127 340/605 |
| 2011/0230700 A1 * | 9/2011 | Sing ..................... A61N 5/1015 600/7 |
| 2011/0257550 A1 | 10/2011 | Choi |
| 2011/0297696 A1 * | 12/2011 | Casares .................... G07C 1/10 222/52 |
| 2012/0271187 A1 | 10/2012 | Mcneill |
| 2013/0338521 A1 * | 12/2013 | Thompson ............. A61M 39/08 600/532 |
| 2013/0345587 A1 * | 12/2013 | Colman ............. A61M 39/1011 600/532 |
| 2014/0018691 A1 * | 1/2014 | Mcneill ................. A61M 16/04 600/532 |
| 2014/0065602 A1 | 3/2014 | Milton et al. |
| 2015/0099993 A1 * | 4/2015 | Weaver ............. A61M 16/0463 600/531 |

OTHER PUBLICATIONS

PCT Search Report and Written Opinion dated Aug. 11, 2016 for PCT application No. PCT/US2016/023297, 8 pages.
Bhavani Shankar Kodali MD, "Capnography in Emergency Tracheal Intubations", retrieved on Apr. 17, 2015 at <<http://www.capnography.com/new/component/content/article?id=277&itemid=152>>, 2 pages.

* cited by examiner

BREATHING DETECTION APPARATUS

BACKGROUND

In a medical procedure, during which a patient is sedated or under anesthesia, it is important that the patient's airway and the delivery of gases are monitored closely. There are two main types of anesthesia utilized in caring for patients under anesthesia, namely Monitored Anesthetic Care (MAC) and General Anesthesia (GA). The basic description of "monitoring the airway" is really an oversimplified description of capnography, which is the monitoring of the concentration of end tidal carbon dioxide ("$ETCO_2$") or exhaled carbon dioxide ("$CO_2$") of a patient in order to assess the physiological status and/or determine the adequacy of ventilation during anesthesia.

In the MAC method of capnography, the airway of a patient may be monitored while the patient is wearing a nasal cannula or a simple face mask via which a gas, such as oxygen, is administered to the patient. The face mask may be a plastic, possibly a clear plastic that covers the nose and mouth and is secured to the face by an elastic band around the back of the head. The nasal cannula may be inserted into the nares so that the outflow of oxygen, for example, is inhaled by the patient through the nose.

Alternatively, in GA methods, anesthesia may be accomplished without a nasal cannula or face mask, but instead with a breathing circuit that connects the patient to an anesthetic machine and ventilator. This may be accomplished via an inspiratory and expiratory limb of the breathing circuit connected to the patient at a breathing device that terminates at or about the tracheal opening of the patient's lungs.

In some instances, the effects of sedatives, narcotics, and the majority of general anesthetics decrease respiratory drive and can cause brief or prolonged periods of apnea. Because of such a situation, the implementation of capnography increases the margin of safety for delivery of anesthesia.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size, while other figures may depict the same components on a larger scale for the sake of clarity.

DETAILED DESCRIPTION

Overview

This disclosure is directed to an apparatus that may be used in monitoring the presence of and/or concentration of a systemic biomarker, such as $ETCO_2$ or exhaled $CO_2$ of a patient in order to assess the physiological status and/or determine the adequacy of ventilation during anesthesia. The embodiments are described with specificity in order to meet statutory requirements. However, the description itself is not intended to limit the scope of this patent. Rather, the inventors have contemplated that the claimed invention might also be embodied in other ways, to include different elements or combinations of elements similar to the ones described in this document, in conjunction with other present or future technologies.

The breathing detection apparatus described herein may generally include a tubular channel (also called "a sampling line") and a detection unit that has therein an element sensitive to the systemic biomarkers, which biomarkers may include, for example, $ETCO_2$, nitric oxide, moisture, humidity, temperature, acids, ketones, or other gases, elements, or characteristics found in or associated with exhaled human breath. A biomarker that may be particularly useful is $CO_2$, since the average indoor $CO_2$ levels range from 400-2000 ppm, whereas exhaled $CO_2$ levels range around 38,000 ppm.

The tubular channel permits the flow of exhaled breath to go from the patient to an $ETCO_2$ monitoring device, where the $CO_2$ in the breath exhaled by the patient is monitored for the safety of the patient. With respect to the element in the detection unit that is sensitive to systemic biomarkers, the element is configured such that, upon exposure to a predetermined biomarker, such as $ETCO_2$, an indicator is activated so as to indicate that the element has been exposed and the apparatus has been used. This detection feature notifies the operator of the apparatus, e.g., the anesthesiologist, dentist, or other medical personnel, that the particular $ETCO_2$ monitoring line has been used. As such, the indicator of the detection apparatus may help prevent accidental reuse, which could cause infections due to cross contamination. Further, the detection apparatus may also prevent unintentional and unnecessary waste, which occurs due to operators being unsure whether the apparatus was previously used, in which case, the apparatus is generally thrown away due to uncertainty.

In addition to indicating the prior use of the apparatus, the breathing detection apparatus provides other advantages. Features of the breathing detection apparatus provide versatility in use for various situations, including, but not limited to, being connectable to, for example, a nasal cannula, a face mask, and an endotracheal tube or an adapter therefor. Specifically, the detection unit may include a structural feature (described in detail herein below) that accommodates and secures a nasal cannula thereto. Further, an end of the tubular channel is configured to be secured to either a mask or an anesthesia circuit.

More specifically, the structural features of the breathing detection apparatus allow so that, should it become necessary during a procedure to change between any of the means of providing gas flow to the patient, the various connections are easily accommodated with only minimal effort. For example, if a patient is using a face mask, and it is determined that the patient needs to be intubated, an endotracheal tube may be employed and the breathing detection apparatus may be quickly connected to a compatible port on an adapter interposed between the endotracheal tube and the anesthesia circuit. Likewise, if the patient needs to switch from a face mask to a nasal cannula, or vice-versa, the breathing detection apparatus can be easily removed from one and quickly attached to the other. Thus, the breathing detection apparatus may be used in different situations due to the structure of the apparatus.

Sometimes, using the current methods of practice monitoring $ETCO_2$ during a procedure, issues and problems related to reliability, and potentially dangerous situations occur. Moreover, patients may even alternate breathing through the nose and the mouth. In such an instance, a nasal sampling line will not reliably detect exhaled air coming from the mouth. The breathing detection apparatus of the instant application helps to eliminate or minimize the occurrence of such situations. Namely, the breathing detection apparatus helps to avoid kinking or occlusions of the sampling line (which may be crafted from, for example, intravenous catheter or extension tubing). Further, the apparatus may eliminate the situation where sampling line is taped to the patient's facial skin. In some instances, hypodermic needles are broken during current procedures and used to puncture the face mask so as to insert tubing therein and sample the $CO_2$. In such situations, the patient may be subject to a possible cut or abrasion from the broken end of the needle. Accordingly, the embodiments of the breathing detection apparatus of the instant application, as detailed herein, may provide several advantages over the current methods of monitoring $CO_2$.

Multiple embodiments of an apparatus that may be used to achieve the desired effects of the instant application, including the ability to definitively determine whether a $CO_2$ sampling unit has been used, are described herein below with respect to FIGS. 1A-6. Note that throughout the specification the terms "proximal" and "distal" are used several times. Unless otherwise specified, "proximal" refers to the end of the apparatus 100 that is connectable to an $ETCO_2$ monitor 140, and "distal" refers to the opposite end of the apparatus 100.

Detailed Explanation of the Components in the Figures

Figure 1A:
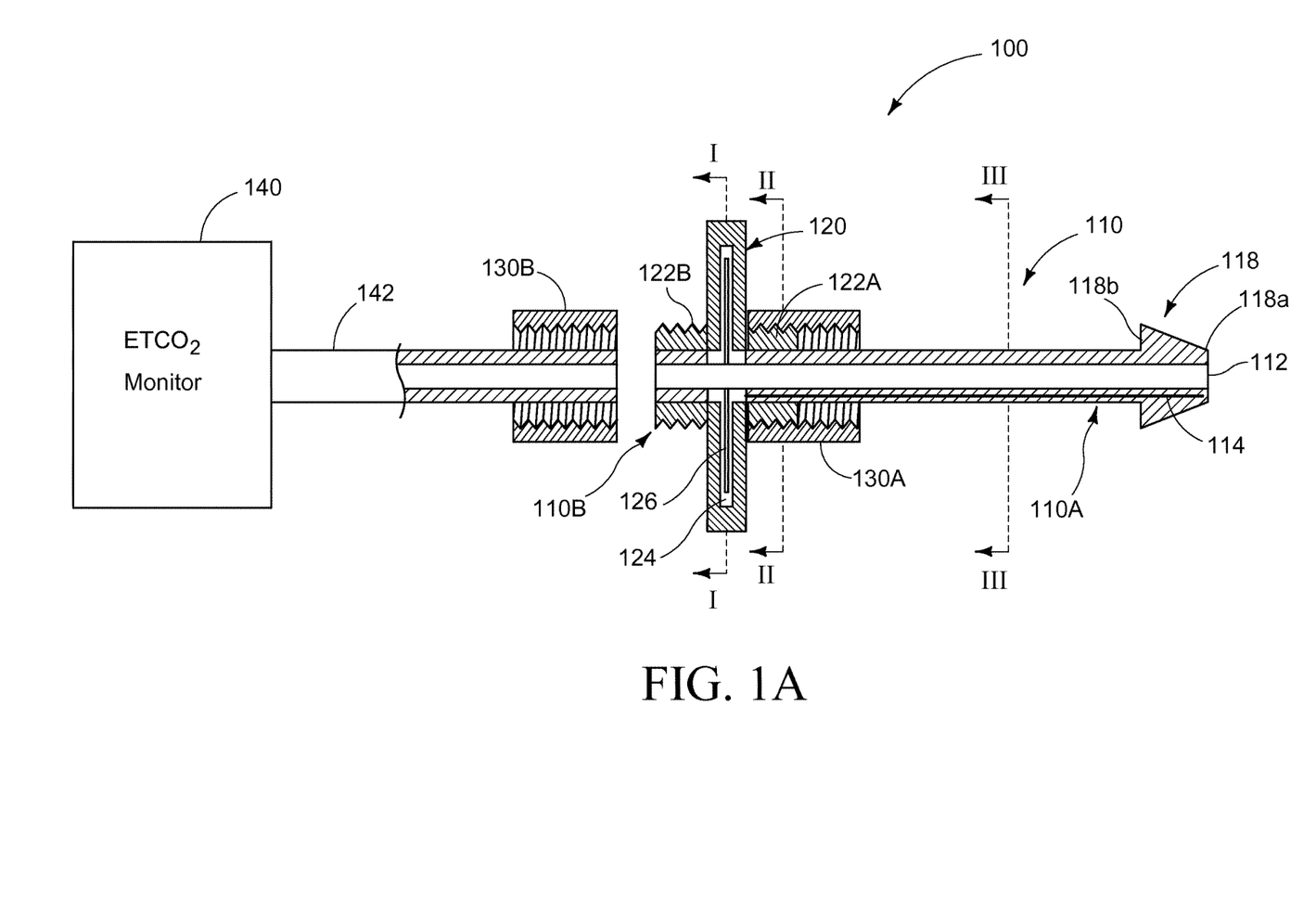
FIG. 1A illustrates a side cross-sectional view of an example of a breathing detection apparatus.

FIG. 1A illustrates an example breathing detection apparatus 100 that may include a sampling tube attachment 110, a detection unit 120, and collars 130A, 130B. In order to monitor the level of $CO_2$, the breathing detection apparatus 100 may be connected to the $ETCO_2$ monitor 140 via an extension tube 142.

The sampling tube attachment 110 has a distal end 110A and a proximal end 110B. The proximal end 110B may be connectable directly or indirectly to the $ETCO_2$ monitor 140. The distal end 110A functions as an intake for exhaled breath via a first lumen 112 that is open to the environment at the distal end 110A. In practice, the distal end 110A is positioned in a location with respect to the patient so as to intake the exhaled breath via a suction force, and thereby sample the $ETCO_2$. The position varies depending on the corresponding apparatus, i.e., nasal cannula, face mask, or endotracheal tube, being used to provide gas to the patient. Accordingly, using the apparatus described herein, the concentration of $CO_2$ may be sampled and the status of the patient may be monitored.

One feature of the sampling tube attachment 110, which assists in positioning the distal end 110A near the mouth and/or nose of the patient is a manipulable member 114 disposed adjacent the first lumen 112 in the sampling tube attachment 110. The manipulable member 114 may include a wire, rod, strip, bar, or another section of metal, plastic, ceramic, rubber, or other suitable material, including weather as described below. For example, manipulable member 114 may have a material that is pliable and/or malleable, so as to allow manipulation of the position, shape, and or direction of the extension of the sampling tube attachment 110, with which the manipulable member 114 may be coupled. Thusly, when used in connection with a nasal cannula, the a position of the sampling tube attachment 110 may be manipulated via the manipulable member 114 to be positioned closer to the mouth or the nose of the patient, or therebetween, in order to intake and allow the patient's breath to pass through the first lumen 112 in the sampling tube attachment 110 to the $ETCO_2$ monitor 140.

Figure 1B:
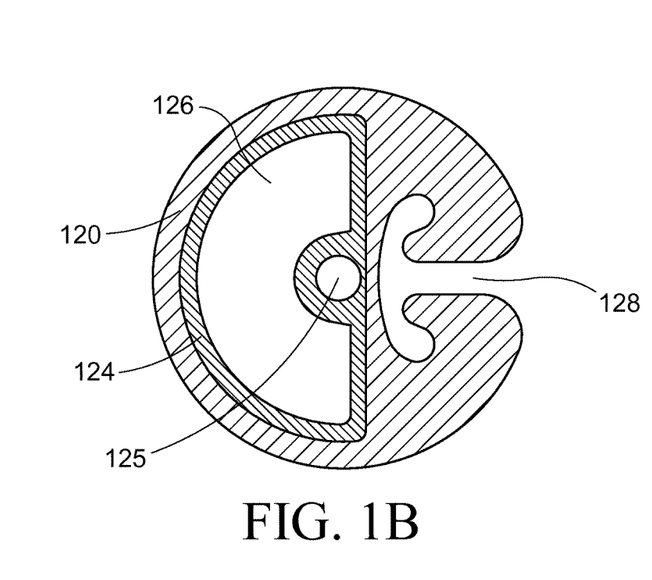
FIG. 1B illustrates a front cross-sectional view at line I-I of the detection unit of the example breathing detection apparatus in FIG. 1A.
Figure 1C:
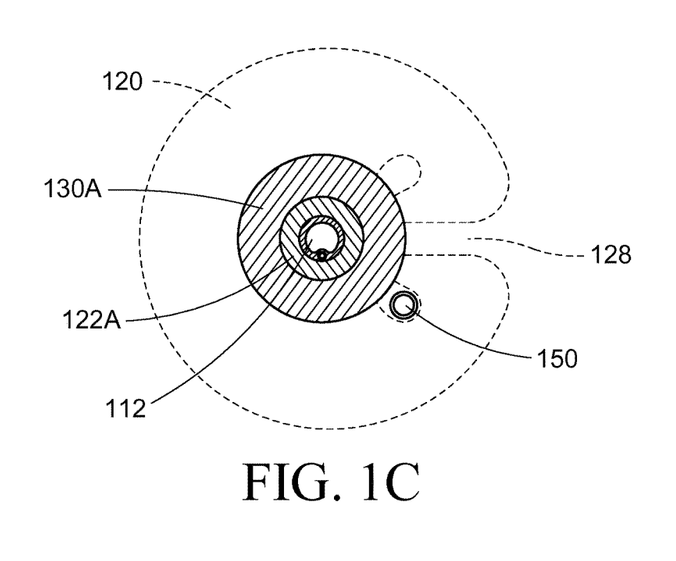
FIG. 1C illustrates another front cross-sectional view at line II-II of a protrusion and collar in front of the chamber of the detection unit of the example breathing detection apparatus in FIG. 1A.
Figure 1D:
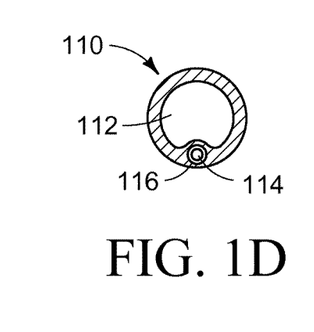
FIG. 1D illustrates another front cross-sectional view at line III-III of a sampling tube attachment in front of the detection unit of the example breathing detection apparatus in FIG. 1A.

Inasmuch as the manipulable member 114 is adjacent the first lumen 112, the manipulable member 114 may be disposed in a second lumen 116 that extends parallel with the first lumen 112, as shown more clearly in FIG. 1D. Alternatively, the manipulable member 114 may be attached directly to an inner surface of the first lumen 112 or an outer surface of the sampling tube attachment 110; or the manipulable member 114 may simply be embedded in the wall of the first lumen 114, as it appears in FIG. 1A. The length of the manipulable member 114 may be such that the manipulable member 114 extends: 1) throughout the entire length of the sampling tube attachment 110; 2) at least along the distal end 110A; or 3) for a portion less than the entire length of the sampling tube attachment 110 and located away from the ends thereof, such as at a middle portion between the distal and proximal ends 110A, 110B.

A tip of the distal end 110A of the sampling tube attachment 110 may have a flange 118. The width of the flange 118 may be tapered. The flange 118 may include an insertion end 118a, which starts at the distal end 110A and may be approximately the same width as the first lumen 112, and an abutting end 118b, which is wider than the insertion end 118a as the flange 118 extends taperingly toward the proximal end 110B, such that the width of the flange 118 is larger at the abutting end 118b at the proximal side than the insertion end 118a at the distal side, as depicted in FIG. 1A.

Figure 4:
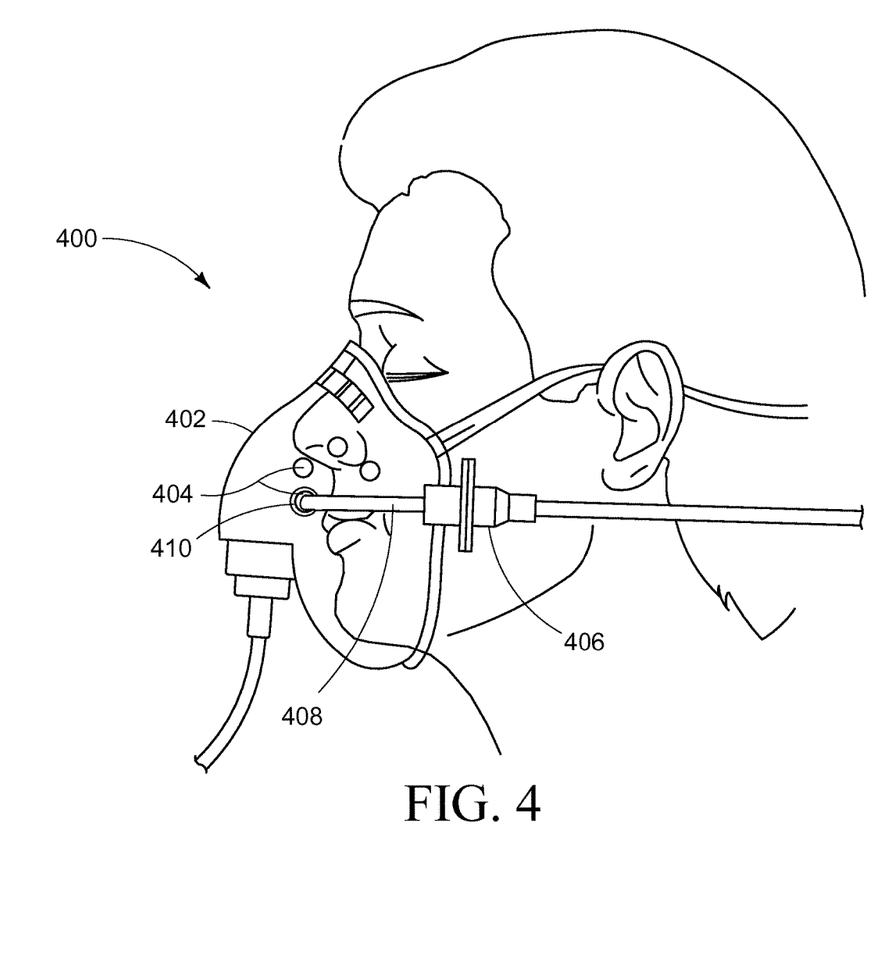
FIG. 4 illustrates a view of an example breathing detection apparatus attached to a face mask.
Figure 5:
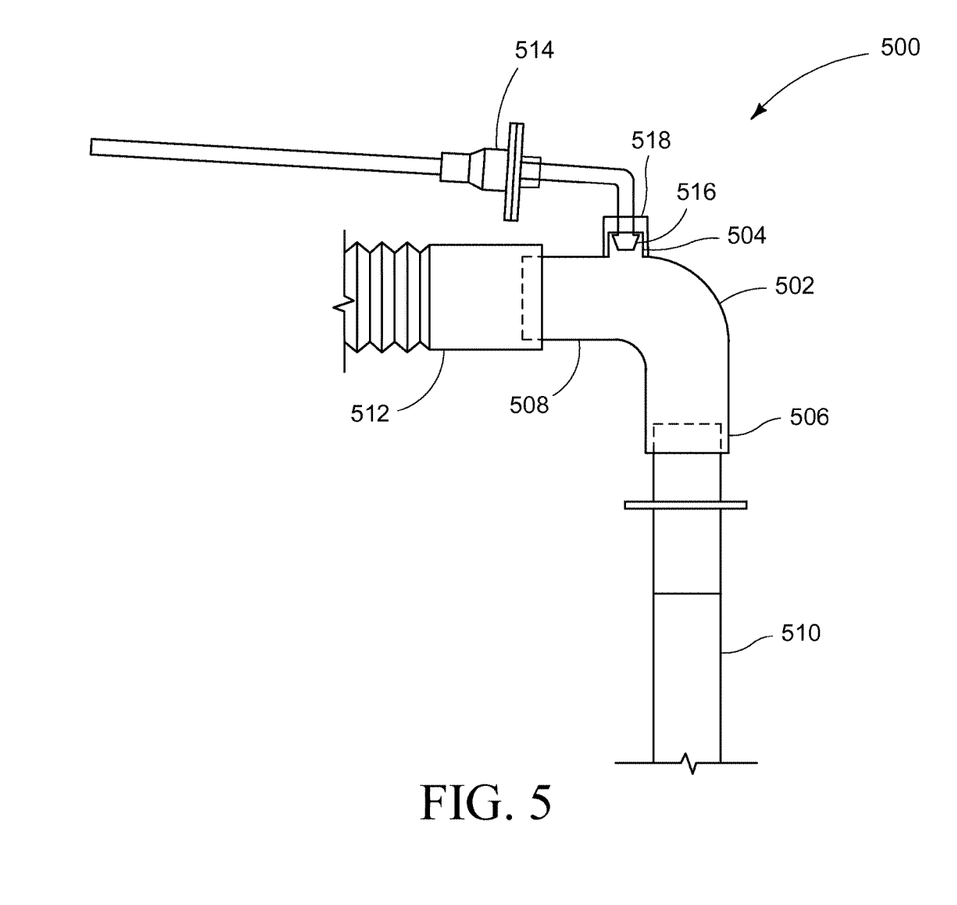
FIG. 5 illustrates an example breathing detection apparatus attached to an adapter on an endotracheal tube.

The abutting end 118b of the flange 118 may be substantially flat and extend in a plane orthogonal to the axis of the first lumen 112, such that, upon inserting the tip of the distal end 110A of the sampling tube attachment 110 into a mask or a port (see, for example, hole 404 on mask 402 in FIG. 4, or port 504 on adapter 502 in FIG. 5), the abutting end 118b abuts an inside surface of the mask or port. (FIGS. 4 and 5 are discussed in greater detail herein below.) Thusly, the abutting end 118b minimizes the chance for accidental extraction of the sampling tube attachment 110 from the mask or port by restricting movement via abutting surfaces.

Turning to the detection unit 120 of the apparatus 100, the detection unit 120 may include a chamber 124 defined by two opposing walls connected at a periphery thereof. The chamber 124 may be sealed from the outside environment with exception of a hole 125 (see FIG. 1B) leading into the chamber 124. The hole 125 may pass through the detection unit 120. Further, the hole 125 may be aligned with the first lumen 112 so as to receive the breath flowing into the first lumen 112.

In an embodiment depicted in FIG. 1A, the detection unit 120 may further include a first protrusion 122A protruding from a wall of the chamber 124, extending toward the distal end 110A of the sampling tube attachment 110, and a second protrusion 122B protruding from the opposite wall of the chamber 124, extending toward the proximal end 110B. As depicted, protrusions 122A and 122B may be tubular bodies having a threaded outer surface. The threaded outer surface of protrusion 122A may connect to collar 130A, which has an inner threaded surface. Likewise, the threaded outer surface of protrusion 122B may connect to collar 130B. Thus, the sampling tube attachment 110 may connect to the monitor 140 via the threaded engagement between protrusion 122B and collar 130B.

The detection unit 120 may further include an element 126 that senses or is sensitive to systemic biomarkers, such as $CO_2$, for example, as discussed above. The element 126 may be configured to experience a permanent change in state upon sensing a predetermined, threshold amount of a biomarker, such as a specific level of $CO_2$ concentration. For the purposes of this application, the term "permanent" means at least until an individual can determine that the apparatus has been used by checking the state of the indicator from element 126. Thus, in an embodiment where the element 126 implements a power source, the term "permanent" would mean until the power source is exhausted. In another embodiment where the element 126 is not electronic, "permanent" means a change of state that is not intermittent or alternating between the original state and the altered state, outside of the intended period of use on a patient. Thus, for example, if the element 126 is a material that changes color, a "permanent" change would be one that would change upon the initial sensing of the threshold amount of the biomarker during the procedure, and which state would not revert to the original state, if ever, until after a length of time after a procedure terminates, during which an individual would have appropriately discarded the used apparatus.

The element 126 may be disposed within the chamber 124, as seen in FIGS. 1A and 1B. Alternatively, depending on the embodiment, element 126 may be embedded within walls of the detection unit 120. For example, the element 126 may be a material (e.g., paper or cloth) that is chemically designed to change color or disintegrate upon being exposed to a predetermined, threshold concentration level of the chosen biomarker. Alternatively, the element 126 may include an electronic device configured to sense the biomarker. In such an embodiment where element 126 includes an electronic device, the electronic device may be configured to actuate an indicator such as an LED, or emit an odor, or produce an audible indication such as a periodic "beeping" sound, upon being exposed to the predetermined level of the biomarker. Accordingly, when the apparatus 100 has been used, an indicator, such as a change in the physical appearance, the smell, or the sound may be actuated or displayed. Therefore, an individual may look at, smell, or listen for the indicator of the element 126 to determine whether the apparatus 100 has been used.

It is noted that, despite the appearance of element 126 in FIGS. 1A and 1B, the depicted shape of a half crescent for the element 126 is intended to represent any or all of the embodiments of an element 126 that senses or is sensitive to a biomarker, such as $CO_2$, either directly or merely as a representation of an element that is accommodated in the detection unit 120. Thus, the half crescent shape of element 126 shown in FIG. 1B may represent a paper such as a material or cloth or an electronic device shaped to fit within the detection unit 120.

In an embodiment of the apparatus, in which the element 126 includes a material, the properties of the material may be such that the material changes color permanently upon exposure to a predetermined level of $CO_2$ or other biomarker. Thus, in this situation, a medical professional may be able to determine whether the apparatus 100 has been used by looking at the color of the material of the element 126 to see if the color has changed from the original state. For example, at the time of manufacture, the original color of the element 126 may be white. Then, after the apparatus 100 is used in a procedure and is thereby exposed to end tidal $CO_2$ or other biomarker, the element 126 may have turned red, as an indication that it has been used. Therefore, the individual would see the element 126 turned red and know that the apparatus was already used.

In an embodiment in which the element 126 is an electronic device, the electronic device may be embedded in the detection unit 120, for example in the chamber 124. The electronic device may have componentry sensitive to a biomarker, which upon exposure to the biomarker may perform any or more than one of the following actions: electrically connect an LED, trigger a switch to emit an odor, and/or trigger a switch to emit audible sound. Thus, multiple indicators may be combined to provide alternative ways of determining that the apparatus has been used. The electronic device may be powered by an internal power source embedded within the detection unit 120 or element 126, or the device may be powered by an external power source that may need to be connected or adjacent to the apparatus 100, for example via wireless power (power sources not explicitly depicted).

FIG. 1B is a cross-sectional view of the detection unit 120 along the line I-I shown in FIG. 1A. As previously mentioned, the detection unit 120 may include a chamber 124 with a hole 125 therethrough, and an element 126. Additionally FIG. 1B shows channel 128, which may be used to secure the breathing detection apparatus 100 to a nasal cannula 150 (seen in FIGS. 1C and 2). Channel 128 may be a passageway into the side of the detection unit 120 and may include a T-like shape having the ends of the "T" extend slightly toward the entrance of the channel 128 and away from the center of the detection unit 120. An individual may use the detection apparatus 100 to place a nasal cannula on either side of the T-like shape to secure the detection apparatus 100 to the nasal cannula. Alternatively, the channel 128 may include only one half of the T-like shape (not depicted), so as to appear similar to a candy cane shape. It is contemplated that other shapes for the channel 128 may be used to secure the detection apparatus 100 to a nasal cannula.

An advantage of using the T-like shape or the candy cane shape for the channel 128 is that after sliding the nasal cannula 150 into the channel 128, collar 130A may be connected to protrusion 122A, which in turn prevents nasal cannula 150 from being able to come out of the detection unit 120. That is, as seen in FIG. 1C, the passage 128 is blocked by collar 130, thereby preventing nasal cannula 150 from being accidentally removed.

It is noted that FIG. 1C and FIG. 1D are cross-sections of the apparatus 100 at lines II-II and III-III, respectively, shown in FIG. 1A.

Additional embodiments of various components shown in FIGS. 1A-1D are discussed herein below.

Figure 2:
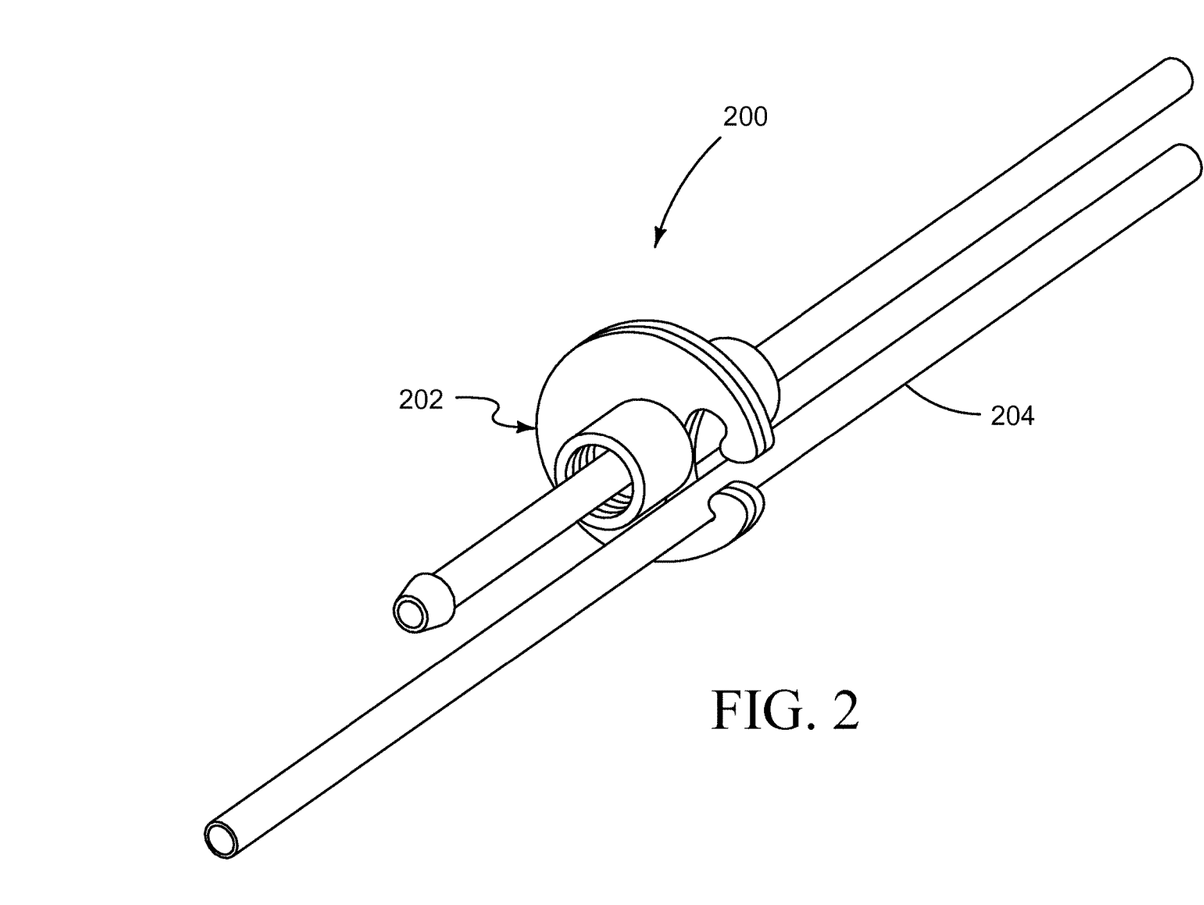
FIG. 2 illustrates an isometric view of an example breathing detection apparatus attached to a nasal cannula.
Figure 3A:
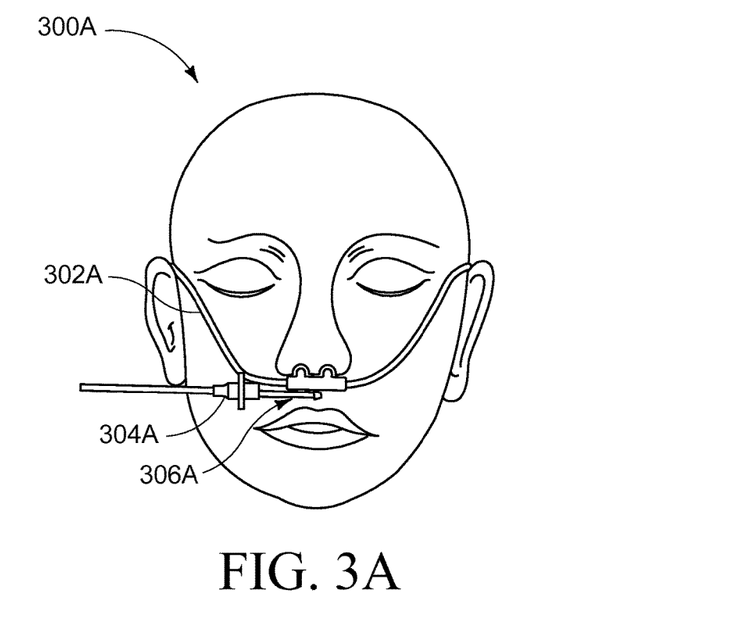
FIG. 3A illustrates an example breathing detection apparatus in use attached to a nasal cannula with the sampling tube attachment in position next to a patient's nose.
Figure 3B:
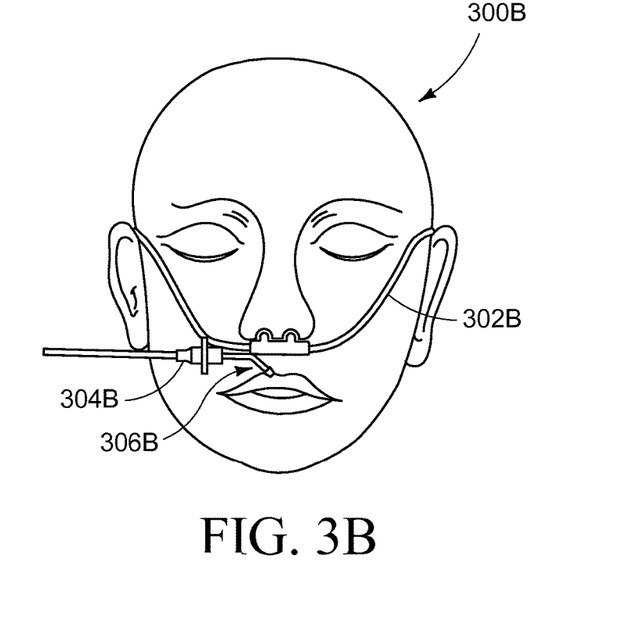
FIG. 3B illustrates an example breathing detection apparatus in use attached to a nasal cannula with the sampling tube attachment in position next to a patient's mouth.

FIG. 2 depicts the assembly 200 of detection apparatus 202 secured to a nasal cannula 204. As discussed above briefly, FIG. 3A depicts position 300A, where nasal cannula 302A is secured to a person and detection apparatus 304A is connected to the nasal cannula 302A. Further, the sampling tube attachment 306A is oriented closer to the nose than to the mouth of the patient. Alternatively, FIG. 3B depicts position 300B, where nasal cannula 302B is secured to a person and detection apparatus 304B is connected to the nasal cannula 302B. Note, however, that the sampling tube attachment 306B is oriented closer to the mouth than to the nose of the patient.

In FIG. 4, a patient is wearing a face mask depicting position 400. The mask 402 may include holes 404, and the detection apparatus 406 is depicted as connected to the mask 402 by way of inserting the distal end of the sampling tube attachment 408 into the mask 402 via flange 410 pushed through one of the holes 404. In this position 400, the width of the flange 410 is larger than the holes 404. Thus, the flange 410 is pushed through the holes 404 and the abutting end of the flange 410 minimizes the risk of accidental removal of the apparatus 406.

FIG. 5 depicts yet another alternative embodiment of position 500, in which the detection apparatus 514 is connected to an adapter 502 by way of inserting the flange 516 into a port 504 on the adapter 502. Furthermore, a first end 506 of the adapter 502 is connected to an endotracheal tube 510. A second end 508 of the adapter 502 is connected to an anesthesia circuit 512. Thus, the flange 516 is sized so as to be engageable with a port 504 of the adapter 502. Note that the collar 518 may be positioned on the port 504 also, so as to assist in securing the distal end of the sampling tube to the adapter 502.

Figure 6A:
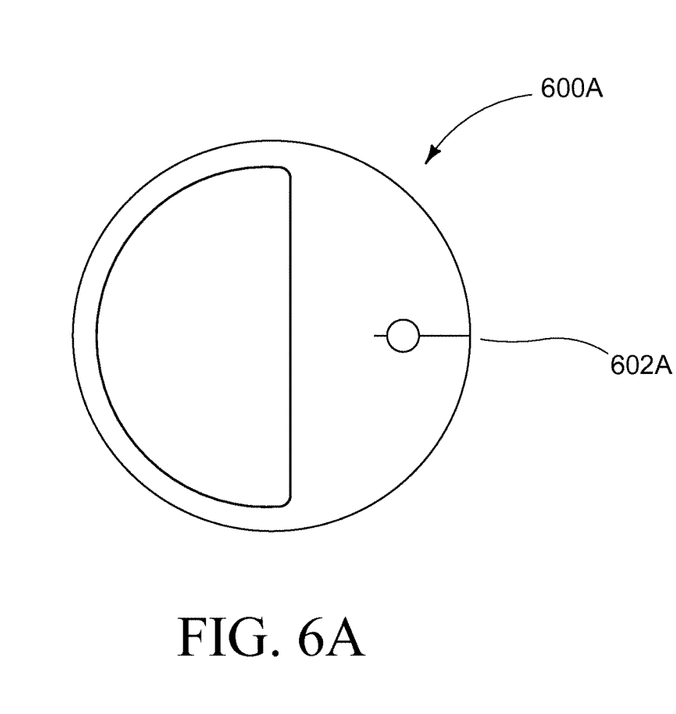
FIG. 6A illustrates an alternative example of a detection unit.
Figure 6B:
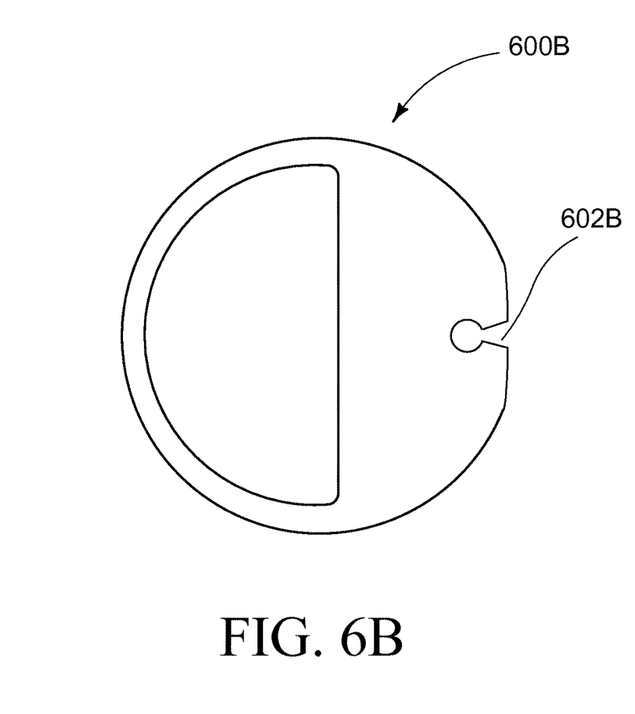
FIG. 6B illustrates another alternative example of a detection unit.

FIGS. 6A and 6B depict alternative embodiments of the detection unit 600A and 600B, respectively. For example, the detection unit 600A does not include a wide passageway from a side of the detection unit 600A to access channel 602A to insert a nasal cannula, as in FIG. 1B. Instead, the side of the detection unit 600A may be, for example, a slit, and the material of the detection unit 600A may be flexible so that unit 600A may be twisted to allow insertion of the nasal cannula. After twisting, the unit 600A will return to the original shape and the cannula should be held in place. Likewise, FIG. 6B shows detection unit 600B with a channel 602B having a width that is less than that of a nasal cannula. In this situation, the nasal cannula may be pinched to squeeze into the channel 602B until the channel opens wide enough for the nasal cannula. Notably, neither of the embodiments in FIGS. 6A and 6B would necessitate the collars 130A, 130B, as in FIG. 1A. Further, the protrusions 122A, 122B would also not be necessary.

Figure 7A:
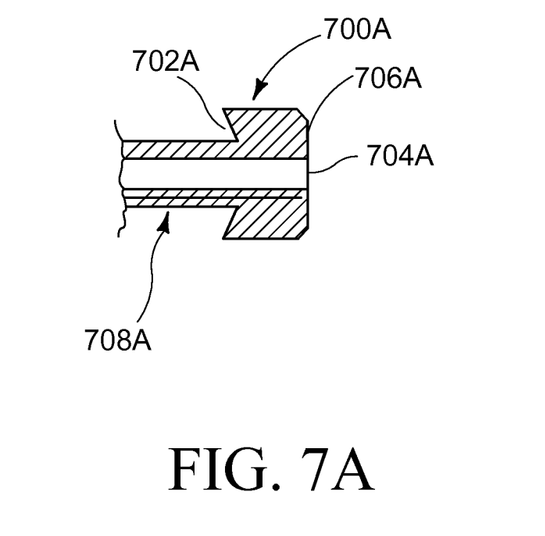
FIG. 7A illustrates an alternative example of a distal tip of the sampling tube attachment.

As an alternative to the continuous tapering of flange 118 of FIG. 1 described above, the flange may be a cylinder-shaped flanged member 700A, (see FIG. 7A) having a nearly uniform outer width. Moreover, flange 700A may include an abutting end 702A, which may be orthogonal as shown in FIG. 1A and described above, or may be tapered inwardly toward the distal end of the first lumen 704A as shown in FIG. 7A, so as to form a ribbed anchor portion, which increases the force required to extract the tube since the ribbed anchor may spread out against the inner wall surface of a mask or port upon an attempt to extract the tube. Thus, the abutting end 702A creates greater surface area contact and greater resistance to extraction. Additionally, in the embodiment shown in FIG. 7A, the distal tip 706A thereof may be sloped or rounded slightly inward so as to ease insertion of the sampling tube attachment 708A into either a mask or a port, as described above.

Figure 7B:
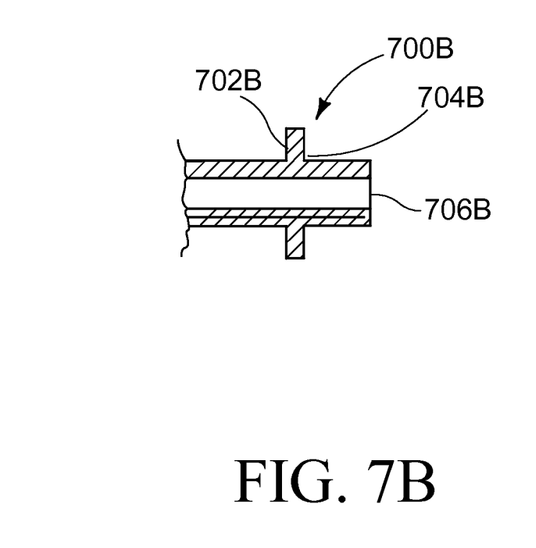
FIG. 7B illustrates another alternative example of a distal tip of the sampling tube attachment.

In yet another alternative embodiment depicted in FIG. 7B, the flange 700B may be a thin-walled, ring-shaped protrusion including an abutting end 702B and a distal end 704B that surrounds the first lumen 706B, either orthogonally to the axis of the first lumen 706B as shown in FIG. 7B, or angled forming a rib as described above, and is set a short way back from the distal tip. In this embodiment, the distal end of the first lumen 706B may be inserted into a mask or port, and then with some additional force applied, the flange 700B may flex backward against the outer wall of the mask or port so as to be pushed through the hole. Then, after passing through the hole, the flange 700B returns to the original position, such that the abutting end 702B abuts the inner wall of the mask or port, and restricts extraction.

Figure 8A:
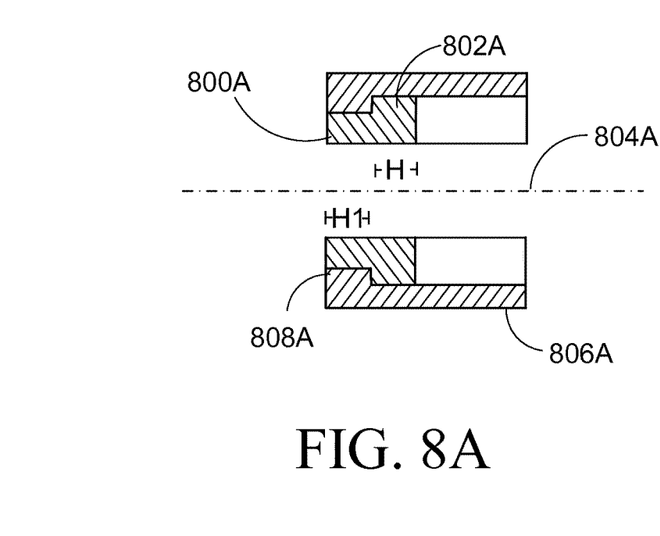
FIG. 8A illustrates an alternative example of a protrusion and collar.

In an alternative embodiment of the protrusions 122A, 122B from FIG. 1A, as seen in FIG. 8A, protrusion 800A (and the protrusion on the opposite side, not pictured) may include a lip flange 802A extending in a radial direction away from the axis of the first lumen 804A, instead of being threaded, as in FIG. 1A. Likewise, the collar 806A (and the collar on the opposite side, not pictured) may include a lip flange 808A extending radially inward toward the axis of the first lumen 804A. The lip flange 802A and lip flange 808A may be sized with respect to each other such that, upon pushing or pulling collar 806A against protrusion 800A, interference exists between opposing walls of the flanges 802A and 808A. In this manner, the collar 806A may be secured to the protrusion 800A via interference, instead of being threaded together. Furthermore, the thickness of the flange 802A in the "H" direction may be adjusted according to the rigidity properties of the material of the protrusion 800A or the lip flange 802A, (which elements may be integral or may form a composite of multiple pieces), so as to be sufficiently rigid to hold the collar 806A in place once connected, yet sufficiently flexible in order to allow the collar 806A to be pushed or pulled over the lip flange 802A under external force. Similarly, the thickness of the flange 808A in the "H1" direction may be adjusted according to the rigidity and elasticity properties of the material of the collar 806A or the lip flange 808A, (which elements may be integral or may form a composite of multiple pieces). Thus, upon pressing the lip flange 808A of the collar 806A against the lip flange 802A of the protrusion 800A, one or both of the lipped flanges 802A and 808A may flex under the applied force so as to allow the collar 806A to slide over the protrusion 800A and lock in place. After sliding into place, due to the elasticity of the materials, one or both of the lip flanges 802A and 808A then return to the original shape/ position, such that opposing surfaces thereof are in abutment. Thusly, the protrusion 800A is engaged and locked with the collar 806A. One manner of achieving this embodiment may include selecting the appropriate materials for the protrusion 800A and the collar 806A. For example, the protrusion at 800A and the collar 806A may include rubber, plastic, or other suitable materials.

Figure 8B:
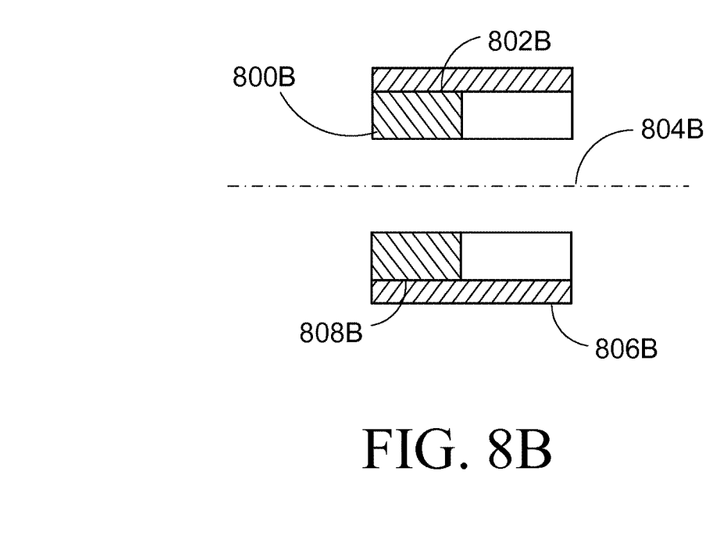
FIG. 8B illustrates another alternative example of a protrusion and collar.

In another alternative embodiment shown in FIG. 8B, protrusion 800B may have a smooth cylindrical outer surface 802B, and collar 806B may be hollow, having a smooth the interior surface 808B. Protrusion 800B and collar 806B are sized such that, when collar 806B is pushed toward protrusion 800B, outer surface 802B of protrusion 800B and interior surface 808B of collar 806B are in close contact, thereby creating an interference fit. The axis of the first lumen 804B passes between the protrusion 800B and the collar 806B. In order to ease insertion of protrusion 800B into collar 806B, the adjacent ends thereof may include a tapered edge. Therefore, in order to connect collar 806B to protrusion 800B, an operator may simply push the collar 806B onto the protrusion 800B.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. An apparatus, comprising:
a tubular channel having a pathway extending between a proximal end and a distal end of the tubular channel, the proximal end being configured to connect directly or indirectly to an end tidal $CO_2$ monitor, and the distal end having an opening;
a detection member including:
a chamber disposed in fluid communication with the pathway of the tubular channel such that gas entering the tubular channel via the opening on the distal end passes into the chamber, and
a detection element disposed within the chamber, the detection element including a component that is sensitive to one or more systemic biomarkers such that, upon exposure to a predetermined concentration level of the one or more systemic biomarkers contained in the gas, a state of the detection element experiences a permanent alteration as an indication that the predetermined concentration level of the one or more systemic biomarkers is present in the gas;
a cannula channel that extends from a side of the detection member in a direction transverse to the pathway of the tubular channel, the cannula channel being configured to allow a nasal cannula to be inserted laterally therein such that the nasal cannula extends in a same direction as the pathway of the tubular channel; and
a movable obstruction element that, in a first position, permits insertion of the nasal cannula into the cannula channel, and when moved from the first position into a second position, impedes removal of the nasal cannula without pinching the nasal cannula when the nasal cannula is inserted in the cannula channel,
wherein the cannula channel includes a slot having a width as wide as a diameter of the nasal cannula and a thickness as thick as the detection member, the slot extending longitudinally from an outer wall of the detection member toward the chamber and curving to extend away from the chamber before terminating within the outer wall of the detection member,
wherein the detection member further includes a protrusion on a side thereof, the protrusion extending around the tubular channel and having a threaded external surface,
wherein the obstruction element is a cylindrical collar having threads on an internal surface, a first side of the collar having a hole therein through which the first end of the tubular channel extends, and a second side of the collar facing the detection member,
wherein, in the first position, the collar is disconnected from the detection member and the nasal cannula is insertable into the slot, and
wherein, in the second position, the collar is connected to the detection member, via engagement between the threads on the internal surface of the collar and the threaded external surface of the protrusion on the side of the detection member, and the nasal cannula is fixed in place via pressure between a sidewall of the slot and an exterior side wall of the collar.

2. The apparatus according to claim 1, wherein the chamber is defined by at least a first wall, a second wall facing the first wall, and an adjoining wall that continuously adjoins the first and second walls, thereby forming the chamber, and
wherein the detection element is disposed between the first and second walls.

3. The apparatus according to claim 1, wherein the alteration of the state of the detection element includes a permanent physical appearance alteration.

4. The apparatus according to claim 3, wherein the physical appearance alteration includes a change in color of the detection element.

5. The apparatus according to claim 3, wherein the physical appearance alteration includes a disintegration of at least a portion of the detection element.

6. The apparatus according to claim 1, wherein the detection member further includes an electronic component, and
wherein the alteration of the state of the detection element triggers an auditory notification from the electronic component.

7. The apparatus according to claim 1, wherein the alteration of the state of the detection element includes an odor-producing alteration, such that, upon sensing the predetermined concentration level of the one or more systemic biomarkers, the detection element triggers a release of an odor.

8. The apparatus according to claim 1, wherein a tip of the distal end includes a tapered flange that increases in taper from the tip toward the proximal end.

9. The apparatus according to claim 1, wherein a direction of extension, a peripheral shape of the tubular channel, or both are adjustable.

10. The apparatus according to claim 1, wherein a wall of the tubular channel includes a manipulable member extending in the wall.

11. An apparatus, comprising:
a tube having a first end and a second end, the tube including:
a first lumen that is open at the first end, and
a second lumen having a manipulable member therein;
a detection unit that attaches to the second end of the tube, the detection unit including:

a chamber disposed in fluid communication with the first lumen of the tube, and a biomarker-reactive element disposed within the chamber, the biomarker-reactive element including a component such that, upon exposure to a gas having a threshold concentration level of a pre-determined biomarker, a state of the biomarker-reactive element permanently changes as an indication that the threshold concentration level of the pre-determined biomarker is present in the gas;

a cannula channel that extends from a side of the detection unit in a direction transverse to the pathway of the tubular channel, the cannula channel being configured to allow a nasal cannula to be inserted laterally therein; and a movable obstruction element that, in a first position, permits insertion of the nasal cannula into the cannula channel, and when moved from the first position into a second position, impedes removal of the nasal cannula without pinching the nasal cannula when the nasal cannula is inserted in the cannula channel, wherein the cannula channel includes a slot having a width as wide as a diameter of the nasal cannula and a thickness as thick as the detection unit, and the slot extending longitudinally from an outer wall of the detection unit toward the chamber and curving to extend away from the chamber before terminating within the wall, wherein the detection unit further includes a protrusion on a side thereof, the protrusion extending around the tube and having a threaded external surface, wherein the obstruction element is a cylindrical collar having threads on an internal surface, a first side of the collar having a hole therein through which the first end of the tube extends, and a second side of the collar facing the detection unit, wherein, in the first position, the collar is disconnected from the detection unit and the nasal cannula is insertable into the slot, and wherein, in the second position, the collar is connected to the detection unit, via engagement between the threads on the internal surface of the collar and the threaded external surface of the protrusion on the side of the detection unit, and the nasal cannula is fixed in place via pressure between a sidewall of the slot and an exterior side wall of the collar.

12. The apparatus according to claim 11, wherein a cross-section profile of an exterior frame of the detection unit is generally disc-shaped, wherein the protrusion of the detection unit is a first cylindrical protrusion, and the detection unit further includes a second cylindrical protrusion, the first and second cylindrical protrusions extending, respectively from opposite sides of the disc-shaped frame, and wherein the hole extends through each of the first and second cylindrical protrusions and a center portion of the detection unit such that the hole leads into and out of the chamber.

13. The apparatus according to claim 12, wherein an exterior surface of the respective first and second cylindrical protrusions includes helical threads thereon, wherein the obstruction element is a first cylindrical collar, wherein the apparatus further comprises a second cylindrical collar, and wherein each of the first collar and the second collar have an internally threaded surface that is engageable with the helical threads of the exterior surface of the first and second cylindrical protrusions, respectively, the first collar surrounding the tube so as to engage the first cylindrical protrusion of the detection unit, and the second collar being engageable with the second cylindrical protrusion so as to secure a sample tube, which is connected to an end tidal $CO_2$ monitor, to the detection unit.

14. The apparatus according to Claim 13, wherein, when viewed from a perspective of the disc-shaped cross-section profile of the detection unit, the biomarker-reactive element is positioned within at least a portion of a first half of the disc-shaped detection unit, and wherein a second half of the disc-shaped cross-section profile includes the cannula channel including a slot extending into a center portion thereof, the slot branching into one or more slot branches that extend transverse to a direction of extension of the slot, and a width of the slot and slot branches accommodating a diameter of the nasal cannula.

15. The apparatus according to claim 14, wherein the one or more slot branches extend back toward an outer perimeter of the exterior frame of the detection unit, and wherein a size of an outer diameter of the first collar is such that, when the first collar is engaged with the first protrusion and the nasal cannula is inserted into a slot branch, an outer surface of the first collar contacts a surface of the nasal cannula and blocks the slot branch so that the nasal cannula cannot be removed.

16. The apparatus according to claim 11, wherein the first end of the tube includes a flange on a tip thereof, the flange being tapered so as to be a same width as a width of the tube at the tip and tapering out to be larger than the width of the tube toward the detection unit.

17. The apparatus according to claim 11, wherein, upon exposure to the threshold concentration level of a predetermined biomarker, the biomarker-reactive element changes color, triggers an auditory notification, or emits an odor.

18. An apparatus, comprising:
a tube having a first end and a second end, the tube including:
a first lumen that is open at the first end, and
a second lumen having a manipulable member therein;
a detection unit that attaches to the second end of the tube, the detection unit including:
a chamber disposed in fluid communication with the first lumen of the tube, and
a biomarker-reactive element disposed within the chamber, the biomarker-reactive element including a component such that, upon exposure to a gas having a threshold concentration level of a pre-determined biomarker, a state of the biomarker-reactive element permanently changes as an indication that the threshold concentration level of the pre-determined biomarker is present in the gas;

a cannula channel that extends from a side of the detection unit in a direction transverse to the pathway of the tubular channel, the cannula channel being configured to allow a nasal cannula to be inserted laterally therein; and a movable obstruction element that, in a first position, permits insertion of the nasal cannula into the cannula channel, and when moved from the first position into a second position, impedes removal of the nasal cannula without pinching the nasal cannula when the nasal cannula is inserted in the cannula channel, wherein a cross-section profile of an exterior frame of the detection unit is generally disc-shaped, wherein the detection unit includes first and second cylindrical protrusions extending, respectively from opposite sides of the disc-shaped frame, wherein a hole extends through each of the first and second cylindrical protrusions and a center portion of the detection unit such that the hole leads into and out of the chamber, wherein the tube extends into the chamber through the first cylindrical protrusion, wherein an exterior surface of the respective first and second cylindrical protrusions includes helical threads thereon, wherein the obstruction element is a first cylindrical collar, wherein the apparatus further comprises a second cylindrical collar, wherein each of the first collar and the second collar have an internally threaded surface that is engageable with the helical threads of the exterior surface of the first and second cylindrical protrusions, respectively, the first collar surrounding the tube so as to engage the first cylindrical protrusion of the detection unit, and the second collar being engageable with the second cylindrical protrusion so as to secure a sample tube, which is connected to an end tidal $CO_2$ monitor, to the detection unit, wherein, when viewed from a perspective of the disc-shaped cross-section profile of the detection unit, the biomarker-reactive element is positioned within at least a portion of a first half of the disc-shaped detection unit, wherein a second half of the disc-shaped cross-section profile includes the cannula channel including a slot extending into a center portion thereof, the slot branching into one or more slot branches that extend transverse to a direction of extension of the slot, and a width of the slot and slot branches accommodating a diameter of the nasal cannula, wherein the one or more slot branches extend back toward an outer perimeter of the exterior frame of the detection unit, and wherein a size of an outer diameter of the first collar is such that, when the first collar is engaged with the first protrusion and the nasal cannula is inserted into a slot branch, an outer surface of the first collar contacts a surface of the nasal cannula and blocks the slot branch so that the nasal cannula cannot be removed.

\* \* \* \* \*